United States Patent [19]

Hill

[11] 3,962,297

[45] June 8, 1976

[54] HIGH BURNING RATE CATALYST

[75] Inventor: William E. Hill, Huntsville, Ala.

[73] Assignee: The United States of America as represented by the Secretary of the Army, Washington, D.C.

[22] Filed: Mar. 7, 1969

[21] Appl. No.: 805,385

[52] U.S. Cl. ............... 260/439 CY; 260/429 CY; 149/22
[51] Int. Cl.$^2$ ......................................... C07F 15/02
[58] Field of Search .............. 260/439 CY, 429 CY; 149/22

[56] References Cited
UNITED STATES PATENTS

| | | |
|---|---|---|
| 3,336,377 | 8/1967 | Marcellis et al. ................. 149/22 X |
| 3,375,282 | 3/1968 | Kauffman et al. ................. 149/22 X |
| 3,490,907 | 1/1970 | Schenck et al. ........... 260/439 CY X |

*Primary Examiner*—Harvey E. Behrend
*Attorney, Agent, or Firm*—Nathan Edelberg; Robert P. Gibson; Jack W. Voigt

[57] ABSTRACT

1-isopropenyl-2-ferrocenoylcarborane. This compound may be employed as an acceleration burning rate catalyst in order to promote the burning rates of propellant compositions such as solid composite propellant compositions.

3 Claims, No Drawings

HIGH BURNING RATE CATALYST

BACKGROUND OF THE INVENTION

The desirability of rapid burning propellant compositions for rocket and ordnance projections is well established. Burning rate catalysts have long been employed to achieve rapid burning propellant compositions. Examples of prior art acceleration burning rate catalysts are ferric oxide and copper chromite. Compounds of the ferrocene type have also been used as acceleration burning rate catalysts. Examples are ferrocene, normal-butylferrocene and a wide variety of other ferrocene compounds. Other compounds and compositions, such as decaborane, alkyldecaboranes mixtures such as HEF-3 (consisting on a weight basis of 67% monoethyldecaborane, 26% diethyldecaborane, 2.5% triethyldecaborane, and 4.5% decaborane), and isopropenylcarborane have also been employed as catalysts for use in propellant compositions. For further information about the use of the above type compounds refer to U.S. Pat. No. 3,386,869.

Thus, a constant need exists in solid propellant rocketry for continued improvement to fuels, binders, processing aids, and catalysts to promote burning. This invention is concerned with a means for increasing the burning rate of the propellant composition, and particularly, the catalyst which provides the means.

An object of this invention is to provide a novel acceleration burning rate catalyst for use in a propellant composition.

A particular object of this invention is to provide such a catalyst of the ferrocene type combined in a carborane compound.

SUMMARY OF THE INVENTION 1-isopropenyl-2-ferrocenoylcarborane may be employed as an acceleration burning rate catalyst in order to promote the burning rates of propellant compositions such as solid composite propellant compositions.

DESCRIPTION OF THE PREFERRED EMBODIMENTS 1-isopropenyl-2-ferrocenoylcarborane may be employed in propellant compositions in amounts of from about 1% to about 10% by weight as an acceleration burning rate catalyst in order to improve the burning rates of the propellant compositions.

1-isopropenyl-2-ferrocenoylcarborane is a new compound having the following structure:

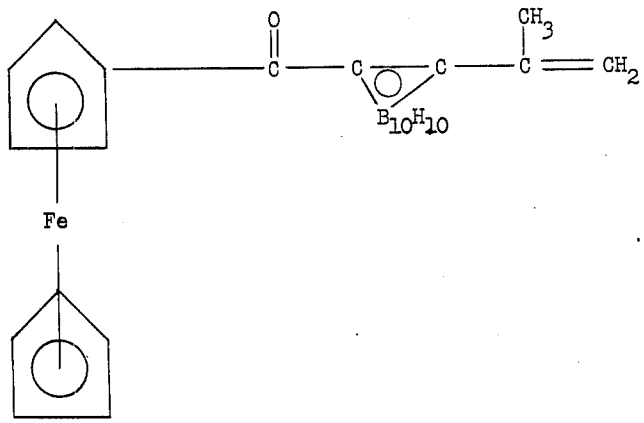

1-isopropenyl-2-ferrocenoylcarborane can be synthesized according to the following procedure:

An equimolar amount of ferrocenoyl chloride and lithio-isopropenylcarborene are mixed in diethyl ether at reflux temperature and allowed to reflux for one hour. The reaction mixture is then quenched with water. After shaking the mixture, the water layer is removed and discarded. The ether is removed under vacuum. The dark red oil obtained is eluted over silica gel yielding the desired solid product 1-isopropenyl-2-ferrocenoylcarborane ($FeC_{16}H_{24}B_{10}O$) Calculated for $FeC_{16}H_{24}B_{10}O$: % C for this compound is 48.50. The % C found is 49.00. The calculated %H for this compound is 6.06. The % H found is 5.98.

The present invention makes use of the above described isopropenylcarborane-ferrocene compound as a catalyst for solid propellant compositions. Thus, the desirable catalytic properties of the carborane and ferrocene catalysts are made available in the same molecule. The catalyst compound of this invention has properties which are desirable for the described application; these properties include the following characteristics: easily blendable with other propellant ingredients, remain distributed in a composition without migration, low volatility, and burnable at a controlled rate in a propellant composition when subjected to a wide range of environmental pressures.

The product, 1-isopropenyl-2-ferrocenoylcarborane, was used in solid, composite propellant compositions in an amount of about 5% by weight of the total propellant weight to test the effect on the burning rate. The burning rate was increased as shown by the following table showing the burning rates of uncured straw propellant compositions A, B, C, and D.

|  | A control | B novel | C control | D novel |
|---|---|---|---|---|
| Formulation, wt. % | | | | |
| carboxy-terminated polybutadiene | 22 | 17 | 45 | 40 |
| Ammonium perchlorate (15$\mu$) | 78 | 78 | — | — |
| Ammonium perchlorate (100$\mu$) | — | — | 55 | 55 |
| 1-isopropenyl-2-ferrocenoylcarborane | — | 5 | — | 5 |
| Properties: | | | | |
| Burning rate (in./sec.) at 500 psi | 0.43 | 0.82 | 0.18 | 0.24 |
| Burning rate (in./sec.) at 1000 psi | 0.60 | 1.00 | 0.26 | 0.32 |
| Burning rate (in./sec.) at 1500 psi | 0.77 | 1.15 | 0.34 | 0.42 |
| Burning rate (in./sec.) at 2000 psi | 0.87 | 1.25 | 0.41 | 0.48 |

The propellant compositions in which the novel acceleration burning rate catalyst of this invention is employed usually contains an oxidizing material and a combustible organic resin fuel.

The oxidizing material is usually an inorganic oxidizing salt. Metal salts, such as potassium perchlorate, are often used; however, upon combustion they form solid particles which create large quantities of visible smoke. Smoke is highly undesirable for military purposes of concealment. Metallic salts useful in such propellant compositions are considerably more expensive than the corresponding ammonium salts. Hence, non-smoking, non-metallic, inorganic oxidizing salts such as hydrazine and ammonium salts are preferred in such applications.

Inorganic oxidizing salts useful in the practice of this invention are nonmetallic chlorate, perchlorate and nitrate salts such as ammonium nitrate, ammonium chlorate, ammonium perchlorate and hydrazine nitrate. The inorganic oxidizing salt or other oxidizing material, in a finely divided condition, is dispersed throughout the fuel component of the propellant. Ordinarily, the oxidizer is present in an amount of from about 45% to about 90% by weight of the total propellant composition.

Combustible organic resinous fuels useful in the practice of this invention include: asphalt, polymers of copolymers of alkenes, arylalkenes, alkynes, alkenyl diglycols, alkyl alkenoates, alkenyl alkenoates, alkenoamides, and amido-alkenyls, and unsaturated alkyd resins heteropolymerized with the above compounds. Ordinarily, the fuel is present in an amount of from about 10% to about 35% by weight of the propellant composition.

The particular fuel employed in the propellant composition does not affect the function of the acceleration burning rate catalyst of this invention. In addition to the type of propellant compositions described above, this catalyst can also be used in propellant compositions utilizing fuel components such as polymers of nitroalkenes, nitroalkynes, nitro-containing acids and their esters, as well as other combustible organic polymeric materials.

The acceleration burning rate catalyst herein described is usually incorporated into the propellant compositions in finely divided form and is mixed with the fuel and other ingredients at the same time the oxidizer is mixed. Thus, in preparing the propellant compositions used with the novel acceleration burning rate catalyst of this invention, the various monomers, oxidizer, burning rate catalyst and a polymerization catalyst, together with any other ingredients desired, are mixed together until a homogeneous mixture is obtained, and then the mixture is cured in a mold by heating. Typically, heating at a temperature of about 80°C. for a period of about 5 days is sufficient to form the desired final propellant composition.

The polymerization catalysts usually employed in such propellant compositions are organic peroxides such as benzoyl peroxide, lauryl peroxide, acetobenzoyl peroxide, ditertiary butyl peroxide, methyl ethyl ketone peroxide, 1-hydroxy-cyclohexyl hydroperoxide, cumene hydroperoxide, and cycloalkane hydrocarbon peroxide, and peresters such as tertiary butyl perbenzoate and diperphthalate.

Various other ingredients can also be added for specific purposes without departing from the scope of the invention. For example, lecithin can be added to improve the castability of the uncured propellant. t-Butyl cathecol or cobalt 2-ethyl hexanoate is often added as a polymerization modifier.

I claim:

1. 1-isopropenyl-2-ferrocenoylcarborane.
2. The method of producing the compound, 1-isopropenyl-2-ferrocenoylcarborane, comprising the steps of:
    a. mixing predetermined amounts of ferrocenoyl chloride and lithio-isopropenylcarborene in diethyl ether at reflux temperature to form a reaction mixture;
    b. refluxing said reaction mixture for one hour;
    c. quenching said reaction mixture with water, shaking quenched reaction mixture, and separating the resulting water layer from the ether layer;
    d. removing ether under vacuum; and
    e. eluting a remaining dark red oil over silica gel to yield the solid product, 1-isopropenyl-2-ferrocenoylcarborane.
3. The method of claim 2 wherein said predetermined amounts are an equimolar amount of said ferrocenoyl chloride and an equimolar amount of said lithio-isopropenylcarborene.

* * * * *

UNITED STATES PATENT OFFICE
CERTIFICATE OF CORRECTION

PATENT NO. : 3,962,297
DATED : June 8, 1976
INVENTOR(S) : William E. Hill

It is certified that error appears in the above–identified patent and that said Letters Patent are hereby corrected as shown below:

In column 1, after the title of invention, "High Burning Rate Catalyst," the following should have been printed:
--DEDICATORY CLAUSE
The invention described herein may be manufactured, used, and licensed by or for the Government for governmental purposes without the payment to me of any royalties thereon.--.

Signed and Sealed this

Twenty-sixth Day of October 1976

[SEAL]

Attest:

RUTH C. MASON
Attesting Officer

C. MARSHALL DANN
Commissioner of Patents and Trademarks